(12) United States Patent
Nagar et al.

(10) Patent No.: US 11,529,333 B2
(45) Date of Patent: Dec. 20, 2022

(54) ORAL PHARMACEUTICAL COMPOSITION COMPRISING ZONISAMIDE AND PROCESS OF PREPARATION THEREOF

(71) Applicant: Azurity Pharmaceuticals, Inc., Woburn, MA (US)

(72) Inventors: Swati Nagar, Amreli (IN); Sandip P. Mehta, Ahmedabad (IN); Manish Umrethia, Ahmedabad (IN); Jayanta Kumar Mandal, Ahmedabad (IN); Sandeep Pal, Ahmedabad (IN)

(73) Assignee: AZURITY PHARMACEUTICALS, INC., Woburn, MA (US)

( * ) Notice: Subject to any disclaimer, the term of this patent is extended or adjusted under 35 U.S.C. 154(b) by 276 days.

(21) Appl. No.: 16/354,764

(22) Filed: Mar. 15, 2019

(65) Prior Publication Data

US 2019/0209529 A1 Jul. 11, 2019

Related U.S. Application Data

(63) Continuation of application No. PCT/IB2018/000901, filed on Aug. 18, 2018.

(30) Foreign Application Priority Data

Aug. 19, 2017 (IN) .............................. 201721029415

(51) Int. Cl.
| | | |
|---|---|---|
| *A61K 31/423* | (2006.01) | |
| *A61K 9/00* | (2006.01) | |
| *A61K 9/10* | (2006.01) | |
| *A61K 47/36* | (2006.01) | |
| *A61K 47/38* | (2006.01) | |
| *A61K 47/12* | (2006.01) | |
| *A61K 47/24* | (2006.01) | |
| *A61K 47/26* | (2006.01) | |

(52) U.S. Cl.
CPC .......... *A61K 31/423* (2013.01); *A61K 9/0053* (2013.01); *A61K 9/0095* (2013.01); *A61K 9/10* (2013.01); *A61K 47/12* (2013.01); *A61K 47/24* (2013.01); *A61K 47/26* (2013.01); *A61K 47/36* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 4,788,220 | A | 11/1988 | Mody et al. |
| 5,272,137 | A | 12/1993 | Blase et al. |
| 2007/0208069 | A1 | 9/2007 | Krishnan et al. |
| 2008/0260837 | A1 | 10/2008 | Namburi et al. |
| 2008/0274196 | A1* | 11/2008 | Jayanthi ............... A61K 9/1623 424/489 |
| 2011/0166225 | A1 | 7/2011 | Verma et al. |
| 2016/0089437 | A1 | 3/2016 | Hsiao |
| 2016/0287594 | A1 | 10/2016 | Gupta et al. |
| 2017/0172961 | A1* | 6/2017 | Heller .................. A61C 19/063 |

FOREIGN PATENT DOCUMENTS

| | | |
|---|---|---|
| EP | 1683516 B1 | 6/2010 |
| EP | 2497467 A1 | 9/2012 |
| IN | 201621039392 A | 5/2018 |
| WO | WO-02094220 A1 | 11/2002 |
| WO | WO-2009082038 A2 | 7/2009 |
| WO | WO-2018067401 A1 | 4/2018 |
| WO | WO-2019038584 A1 | 2/2019 |
| WO | WO-2020039263 A3 | 4/2020 |

OTHER PUBLICATIONS

Nahata, Long-term Stability of Zonisamide, Amitriptyline, and Glycopyrrolate in Extemporaneously Prepared Liquid-dosage Forms at Two Temperatures, Int J Pharm Compd, Mar.-Apr. 2016;20(2):164-6.*
Allen, Monthly Compounding Update, www.uspharmacist.com, Nov. 13, 2015, printed from https://www.uspharmacist.com/monthly_compounding_update/nl/57830/, 2 pages.*
Medisca, Suggested Flavoring Reference Chart, www.medisca.com, Apr. 17, 2016, printed from https://web.archive.org/web/20160417002400/https://www.medisca.com/Files/ReferenceCharts/Suggested%20Flavoring%20Reference%20Chart%20-%20MUS%20&%20MCA.pdf, 1 page.*
www.mystrica.com, 0.1M Citric acid-Sodium citrate buffer buffer—pH range 3.0-6.2, Jul. 25, 2016, printed from https://web.archive.org/web/20160725015105/http://www.mystrica.com/Pages/Applications/citratebuffer.pdf, 1 page.*
Dainippon Sumitomo Pharma, Notice of launching of a new Parkinson's disease drug "TRERIEF", https://www.ds-pharma.com, Mar. 13, 2009, printed from https://www.ds-pharma.com/ir/news/pdf/ene20090313.pdf, 2 pages.*
"ABOBO, Cyril V. et al., "Stability of zonisamide in extemporaneously compounded oral syspensions" Database Medline US National Library of Medicine (NLM, Bethesda, MD (2009)".
"Allen, Loyd, et al. "Zonisamide 10-mg/ml oral suspension" International Journal of Pharmaceutical compounding, International Journal of Pharmaceutical Compounding, US, vol. 13, No. 5, (2009), p. 437".
"Ferreira, A O. et al., "Feasibility of amlodipine besylate, chloroquine phosphate, dapsone, phenytoin, pyridoxine hydrochloride, sulfadiazine, sulfasalazine, tetracycline hydrochloride, trimethoprim an dzonisamide in SyrSpend SF PH4 oral suspensions" Journal of Pharmaceutical an dBiomedical Analysis, vol. 118, (2015), pp. 105-112".
"International Search Report and Written Opinion for PCT Application No. PCT/IB2018/000901 dated Jan. 18, 2019."

(Continued)

*Primary Examiner* — Gigi G Huang
(74) *Attorney, Agent, or Firm* — Wilson Sonsini Goodrich & Rosati

(57) ABSTRACT

The present invention relates to the pharmaceutical composition comprising Zonisamide and one or more pharmaceutically acceptable excipients and also relates to the process for the preparation of the pharmaceutical composition comprising Zonisamide.

13 Claims, No Drawings

(56) References Cited

OTHER PUBLICATIONS

"Kitano, Y, et al., "Anticonvulsant and neuroprotective effects of the novel nootropic agent nefiracetam on kainic acid-induced seizures in rats" Brain Research, Elsevier, Amsterdam, NL. vol. 1057, No. 1-2, (2005), pp. 168-176".

"Nahata, Milap C. "Long-term Stability of Zonisamide, Amitriptyline, and Glycopyrrolate in Extemporaneously Prepared Liquid-dosage Forms at Two Temperatures", International Journal of Pharmaceutical Compounding, vol. 20, No. 2 (2016)".

* cited by examiner

ORAL PHARMACEUTICAL COMPOSITION COMPRISING ZONISAMIDE AND PROCESS OF PREPARATION THEREOF

CROSS REFERENCE TO RELATED APPLICATIONS

This application is a continuation of International Application No. PCT/IB2018/000901 filed Aug. 18, 2018, which claims priority to Indian provisional application Serial No. IN201721026411 filed Aug. 19, 2017. Each of which are hereby incorporated by reference in their entireties.

FIELD

The present invention relates, in general, to the pharmaceutical field, and more precisely it relates to a pharmaceutical composition for the oral administration of Zonisamide and to the process for the preparation thereof. In particular, the present invention relates to the oral liquid composition comprising Zonisamide.

BACKGROUND

Zonisamide, chemically known as 1, 2-benzoxazol-3-ylmethanesulfonamide having an empirical formula $C_8H_8N_2O_3S$ and a molecular weight of 212.2 gm/mol has a following structural formula:

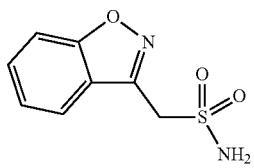 [SMILES: NS(=O)(=O)Cc1noc2ccccc12]

Zonisamide is a benzisoxazole derivative, originally synthesized in Japan in 1974 during exploratory research on psychiatric drugs, where it was subsequently identified as having anticonvulsant activity during screening. Zonisamide is thought to act through its blocking of voltage-dependent sodium channels, reduction of voltage-dependent T-type inward calcium currents, binding to the gamma-aminobutyric acid (GABA)-benzodiazepine receptor complex, and facilitation of both dopaminergic and serotonergic neurotransmission. Zonisamide was approved in Japan in 1989 as both monotherapy and adjunctive therapy for children and adults with generalized or partial seizures. Zonisamide was approved in 2000 in the USA as adjunctive therapy in the treatment of partial seizures in adults with epilepsy. For epilepsy, most studies have used oral zonisamide in daily doses ranging from 200 to 600 mg/day, divided in 2 daily doses, adjusted to maintain serum levels of 15 to 40 μg/ml. Zonisamide is also proposed for treatment of other disease like tardive dyskinesia. It is to be sold, when combined with bupropion, under the brand name empatic for obesity. Zonisamide has been studied for and used as a migraine preventative medication, and has also been shown to be effective in some cases of neuropathic pain. It has also been used off-label by psychiatrists as a mood stabilizer to treat bipolar depression.

EP 2301537 describe a composition comprising zonisamide or a pharmaceutically acceptable salt thereof for use in reducing the weight of an obese subject.

EP 2285374 describe a composition comprising a combination of at least two compounds chosen from the group consisting of zonisamide, dyphylline, tadalafil, argatroban, acamprosate, cinacalcet, terbinafine, cilostazol, baclofen, phenformin, amlodipine and sulfisoxazole, or salts or prodrugs or derivatives or sustained release formulations thereof, for simultaneous, separate or sequential administration.

EP 2222296 and EP 2164487 describe a pharmaceutical composition comprising an AMPA receptor antagonist, Zonisamide and one or more pharmaceutically acceptable carriers. EP1683516 describes a stable pharmaceutical dosage form comprising, in intimate mixture, solid particulate zonisamide and at least one pharmaceutically acceptable excipient.

EP1913935 describes a process for preparing a stable zonisamide pharmaceutical composition, comprising subjecting zonisamide to wet granulation with a granulation liquid to form a granulated mixture as the stable zonisamide pharmaceutical composition wherein the granulation liquid is selected from purified water, alcohol and mixtures thereof.

EP1656094 describes a method of improving the safety of patients receiving zonisamide treatment for epileptic seizures comprising providing a patient with a therapeutically effective amount of zonisamide, and informing the patient that during the course of zonisamide therapy, if (s)he experiences one or more symptoms chosen from the group of abdominal pain, hypovolemia, shock, nausea, anorexia, vomiting, and abdominal distention, to seek immediate medical attention.

EP1503755 describes a method of reducing weight in an overweight subject, said method comprising administering to an overweight subject a pharmaceutical composition comprising zonisamide, in an amount effective to reduce weight in said subject, wherein said weight loss is significant and sustained.

EP1682522 describes a process for the manufacturing of zonisamide compound.

EP1505967 describes use of a first compound and a second compound in the preparation of a medicament for treating obesity in a mammal in need of such treatment, wherein said first compound is bupropion, and said second compound is at least one weight-loss promoting anticonvulsant.

EP1040830 describes a medicament for neurodegenerative diseases comprising zonisamide or an alkali metal salt thereof as an active ingredient.

EP1954241 describes a sustained-release pharmaceutical formulation comprising, zonisamide; and a retardant excipients, wherein the pharmaceutical formulation has a sustained-release dissolution profile comprising at least one dissolution characteristic selected from: (a) Less than 70% of the zonisamide in the sustained-release pharmaceutical formulation is dissolved within a first hour in a standard dissolution test, and (b) Less than 75% of the zonisamide in the sustained-release pharmaceutical formulation is dissolved within a second hour in a standard dissolution test, wherein said pharmaceutical formulation comprises at least 5% by weight of said retardant excipients. EP1411931 describes a method of treating headache in a subject in need of such treatment, said method comprising, administering to a subject a pharmaceutical composition comprising zonisamide, in an amount effective to relieve headache.

Currently Zonisamide is available in oral solid dosage forms like capsule and tablet. Some patient particularly children and the seriously ill persons are not able to swallow solid dosage form. Liquid dosage forms are used fairly commonly by young children or the elders who have trouble swallowing the solid oral dosage forms. Its action is more rapid than solid dosage forms. Therefore there is a need to develop oral liquid dosage form for Zonisamide.

OBJECT OF THE INVENTION

The principal object of the present invention is to provide an oral liquid pharmaceutical composition for Zonisamide.

A further object of the present invention is to provide a process for the preparation of the oral liquid pharmaceutical composition of Zonisamide of the present invention.

A further object of the present invention is to provide composition of Zonisamide for use in adjunctive therapy in the treatment of partial seizures in adults with epilepsy.

SUMMARY

Accordingly, the present invention provides a liquid pharmaceutical composition comprising Zonisamide and one or more pharmaceutically acceptable excipients selected from the group comprising of suspending agent, thickening agent, preservatives, buffering agents, sweetening agents, flavoring agents, vehicles or combinations thereof with improved stability and palatability.

There is also provided a method of preparing the liquid pharmaceutical composition comprising Zonisamide and one or more pharmaceutically acceptable excipients selected from the group comprising suspending agent, thickening agent, preservatives, buffering agents, sweetening agents, flavoring agents, vehicles or combinations thereof.

DETAILED DESCRIPTION

Zonisamide, chemically known as 1, 2-benzoxazol-3-ylmethanesulfonamide having an empirical formula $C_8H_8N_2O_3S$ and a molecular weight of 212.2 gm/mol has a following structural formula:

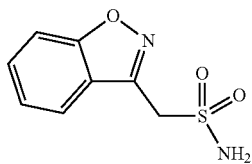 [SMILES: NS(=O)(=O)Cc1noc2ccccc12]

Zonisamide is a benzisoxazole derivative, originally synthesized in Japan in 1974 during exploratory research on psychiatric drugs, where it was subsequently identified as having anticonvulsant activity during screening. Zonisamide is thought to act through its blocking of voltage-dependent sodium channels, reduction of voltage-dependent T-type inward calcium currents, binding to the gamma-aminobutyric acid (GABA)-benzodiazepine receptor complex, and facilitation of both dopaminergic and serotonergic neurotransmission. Zonisamide was approved in Japan in 1989 as both monotherapy and adjunctive therapy for children and adults with generalized or partial seizures. Zonisamide was approved in 2000 in the USA as adjunctive therapy in the treatment of partial seizures in adults with epilepsy. For epilepsy, most studies have used oral Zonisamide in daily doses ranging from 200 to 600 mg/day, divided in 2 daily doses, adjusted to maintain serum levels of 15 to 40 μg/ml. Zonisamide is also proposed for treatment of other disease like tardive dyskinesia. It is to be sold, when combined with bupropion, under the brand name empatic for obesity. Zonisamide has been studied for and used as a migraine preventative medication, and has also been shown to be effective in some cases of neuropathic pain. It has also been used off-label by psychiatrists as a mood stabilizer to treat bipolar depression.

Currently Zonisamide is available in oral solid dosage forms like capsule and tablet. Some patient particularly children and the seriously ill persons are not able to swallow solid dosage form. Liquid dosage forms are used fairly commonly by young children or the elders who have trouble swallowing the solid oral dosage forms. Its action is more rapid than solid dosage forms. Therefore there is a need to develop oral liquid dosage form for Zonisamide.

Therefore, in one of the embodiments, the present invention provides a pharmaceutical composition comprising Zonisamide and one or more pharmaceutically acceptable excipients.

In one of the further embodiments, the pharmaceutical composition comprises Zonisamide and one or more pharmaceutically acceptable excipients selected from the group comprising of suspending agent, thickening agent, preservatives, buffering agents, sweetening agents, flavouring agents, vehicles or combinations thereof.

In one of the further embodiments, the pharmaceutical composition comprises Zonisamide and one or more suspending agent, one or more thickening agent, one or more preservatives, one or more buffering agents, one or more sweetening agents, one or more flavouring agents and one or more vehicles or combination thereof.

In one of the preferred embodiments, the pharmaceutical composition comprises Zonisamide, a suspending agent, a thickening agent, a preservative, a buffering agent, a sweetening agent, a flavouring agent, a vehicle or combination thereof.

In one of the preferred embodiments, the pharmaceutical composition is a liquid pharmaceutical composition.

In one of the preferred embodiments, the liquid pharmaceutical composition is suitable for oral administration.

In one of the further embodiments, the pharmaceutical composition is useful for the manufacture of a medicament.

In one of the further embodiments, the pharmaceutical composition is useful as a medicament.

In one of the further embodiments, the pharmaceutical composition is useful for the manufacture of a medicament in the treatment of partial seizures in adults with epilepsy.

Suspending agents referred in the present invention are the compounds which are added to increase the viscosity of the solution, which is necessary to prevent sedimentation of the suspended particles. Suspending agents also act as thickening agents therefore sometimes they are also referred as thickening agents as well. Examples of suitable suspending agent are but not limited to sodium alginate, methylcellulose, hydroxyethylcellulose, hydroxypropylcellulose, hydroxypropylmethylcellulose, CMC, Na-CMC, microcrystalline cellulose, tragacanth, xanthan gum, bentonite, carageenan, guar gum, colloidal silicon dioxide. The preferred suspending agent is MCC & Na-CMC Dispersion and xanthan gum.

Buffering agents referred in the present invention are the compounds which provide stability and pH control to the pharmaceutical formulations. Examples of suitable buffering agents are but not limited to sodium acetate, sodium citrate, ammonium sulfate, sodium phosphate, disodium hydrogen phosphate, potassium citrate, citric acid monohydrate, trisodium citrate dihydrate. The preferred buffering agents are citric acid monohydrate and trisodium citrate dihydrate.

Preservatives referred in the present invention are the compounds which are included in pharmaceutical dosage form to prevent the growth of microorganisms during the product's manufacture and shelf life. Examples of the suitable preservatives are but not limited to benzyl alcohol, chloro-butanol, chloro-cresol, alkyl esters of paraben, phenol, phenyl ethanol, benzoic acid, potassium sorbate, sodium benzoate etc. and antimicrobial solvents like propylene glycol, chloroform etc. The preferred preservative is sodium benzoate.

Sweetening agents referred in the present invention are the compounds that impart sweetness and improve patient compliance through taste masking. Examples of the suitable sweetening agents are but not limited to sucralose, sucrose, liquid glucose, glycerol, sorbitol, maltitol, saccharin sodium and aspartame. The preferred sweetening agent is sucralose.

Flavouring agents referred in the present invention are the compounds which are added to increase patient acceptance of the drug by masking the specific taste sensations. Examples of suitable flavouring agent are but not limited to essential oils including peppermint oil, orange oil, and lemon oil etc. or can be selected from fruit flavour, e.g. peppermint flavour, strawberry flavour, tutti fruit flavour etc. The preferred flavouring agent is strawberry flavour.

Vehicles referred in the present invention are the liquid bases which carry drug and other excipients in dissolved or dispersed state and can be selected from either aqueous vehicles or oily vehicles. Examples of suitable aqueous vehicles are but not limited to purified water, hydro-alcoholic, polyhydric alcohols and buffers, while suitable examples of oily vehicles are but not limited to vegetable oils, mineral oils, organic oily bases or emulsified bases. The preferred aqueous vehicle is purified water.

Although zonisamide has good wettability, in some embodiments the pharmaceutical composition may benefit from the addition of a wetting agent. Thus, the pharmaceutical composition, particularly the suspensions, may further include a wetting agent. In some embodiments, the wetting agent is selected from alcohol, glycerin, propylene glycol, polyethylene glycol, mineral oil, benzalkonium chloride, benzethonium chloride, cetylpyridinium chloride, docusate sodium, nonoxynol 9, octoxynol, poloxamer, poloxamer 124, poloxamer 188, 237, 338, 407, polyoxyl 35 castor oil, polyoxyl 40 hydrogenated castor oil, polyoxyl 10 oleyl ether, polyoxyl 20 cetylstearyl ether, polyoxyl 40 stearate, polysorbate 20, polysorbate 40, polysorbate 25 60, polysorbate 80, sodium lauryl sulfate, sorbitan monolaurate, sorbitan monooleate, sorbitan monopalmitate, sorbitan monostearate, tyloxapol, and a combination thereof. In some embodiments, the wetting agent is glycerin.

Some embodiments provide a pharmaceutical composition in the form of a suspension for oral delivery comprising zonisamide; water; a suspending agent; and a buffering agent in an amount sufficient to make the composition pH about 3 to about 6. In some embodiments, the suspending agent is xanthan gum at about 3 to about 3.5 mg/mL, although any suitable suspending agent may be used. In some embodiments, the buffering agent is citric acid monohydrate or disodium hydrogen phosphate. Some embodiments further comprise microcrystalline cellulose/sodium carboxymethylcellulose. Some embodiments, may optionally include up to 25 mg/mL glycerin.

In some embodiments, the suspension comprises an active pharmaceutical ingredient which is selected zonisamide; a suspending agent which is about 2 to about 3.5 mg/mL xanthan gum; a buffering agent which is citric acid monohydrate or disodium hydrogen phosphate; 0 to 25 mg/mL glycerin; and microcrystalline cellulose/sodium carboxymethylcellulose.

In one of the further embodiments, the present invention provides process for the preparation of the pharmaceutical composition comprising Zonisamide and one or more pharmaceutically acceptable excipients selected from the group comprising of suspending agent, thickening agent, preservatives, buffering agents, sweetening agents, flavouring agents, vehicles or combinations thereof.

In one of the preferred embodiments, the present invention provides process for the preparation of the pharmaceutical composition comprising Zonisamide by dissolving the preservative, buffering agent and sweetening agent in one part of water while adding the suspending agent, flavouring agent and Zonisamide active ingredient in other part of water, and making up the final volume to required quantity.

In one of the preferred embodiments, the pharmaceutical composition has a pH in between 3.5 and 5.0. In one of the further preferred embodiments, the pharmaceutical composition has a particle size distribution of Zonisamide of D10-13.0 μm, D50-53.0 μm and D90-131.0 μm.

Some embodiments provide a pharmaceutical composition in the form of a suspension for oral delivery comprising zonisamide; water; a suspending agent; a buffering agent; and one or more of a wetting agent and a binder/filler.

In some embodiments, the wetting agent is selected from alcohol, glycerin, propylene glycol, polyethylene glycol, mineral oil, benzalkonium chloride, benzethonium chloride, cetylpyridinium chloride, docusate sodium, nonoxynol 9, octoxynol, poloxamer, poloxamer 124, poloxamer 188, 237, 338, 407, polyoxyl 35 castor oil, polyoxyl 40 hydrogenated castor oil, polyoxyl 10 oleyl ether, polyoxyl 20 cetylstearyl ether, polyoxyl 40 stearate, polysorbate 20, polysorbate 40, polysorbate 25 60, polysorbate 80, sodium lauryl sulfate, sorbitan monolaurate, sorbitan monooleate, sorbitan monopalmitate, sorbitan monostearate, tyloxapol, and a combination thereof. In some embodiments, the wetting agent is glycerin.

In some embodiments, the binder/filler is selected from one or more binders or fillers selected from acacia, agar, alginic acid, carmellose sodium, dextrin, veegum or gel white, gellan gum, sodium alginate, hydroxypropyl starch, maltodextrin, modified starch, pectin, potassium alginate, polyvinyl pyrrolidone, carboxymethyl cellulose or an alkali metal salt thereof, microcrystalline cellulose, bentonite, colloidal silicon dioxide, microcrystalline cellulose/sodium carboxymethylcellulose, and any combination thereof. In some embodiments, the binder/filler is microcrystalline cellulose/sodium carboxymethylcellulose.

Some embodiments provide a pharmaceutical composition in the form of a suspension for oral delivery comprising zonisamide; water; a suspending agent; a buffering agent; and one or more of a wetting agent and a binder/filler. In some instances, the buffering agent is present to yield a pH of about 3 to about 8.

In some embodiments, the suspending agent is selected from gelatin, crosslinked polyacrylic acid, polymethacrylic acid, polyhydroxyethyl methacrylic acid, hydroxypropyl methyl cellulose, polyethylene glycol, sodium carboxymethyl cellulose, hyaluronic acid, chitosan, polycarbophil, pectin, copolymers of dextran, polyacrylamide, acacia, copolymer of caprolactone and ethylene oxide, carbopol 934, tragacanth, eudragit, polyvinyl pyrrolidone, polyacrylate and polyacrylate copolymer resins, celluloses and cellulose derivatives for example methyl-, ethyl- and propyl celluloses; hydroxyalkyl-celluloses, hydroxyl propyl celluloses, hydroxylpropylalkyl celluloses and the like including xanthan gum, polyvinyl resins, polyethylene glycol, polyethylene oxide, sorbitol, sucrose, xylitol, dextrose, fructose, maltitol, sugar, sodium alginate, or a combination thereof.

Some embodiments further include one or more binders or fillers selected from acacia, agar, alginic acid, carmellose sodium, dextrin, veegum or gel white, gellan gum, sodium alginate, hydroxypropyl starch, maltodextrin, modified starch, pectin, potassium alginate, polyvinyl pyrrolidone, carboxymethyl cellulose or an alkali metal salt thereof, microcrystalline cellulose, bentonite, colloidal silicon dioxide, microcrystalline cellulose/sodium carboxymethylcellulose and any combination thereof.

In some embodiments, the buffering agent is acetate, amino acids, ammonium sulfate, benzoate, bicarbonate, borate, citrate, citric acid monohydrate, disodium hydrogen phosphate, glutamate, lactate, meglumine, potassium citrate, sodium acetate, sodium citrate, sodium phosphate, sulfate, tartrate, triethanolamine, TRIS, trisodium citrate dehydrate, and any combination thereof.

Some embodiments provide a pharmaceutical composition in the form of a suspension for oral delivery comprising zonisamide; water; a suspending agent; and a buffering agent in an amount sufficient to make the composition pH about 3 to about 6. In some embodiments the active pharmaceutical ingredient is selected from zonisamide, and primodone. In some embodiments, the suspending agent is xanthan gum at about 3 to about 3.5 mg/mL, although any suitable suspending agent may be used. In some embodiments, the buffering agent is citric acid monohydrate or disodium hydrogen phosphate. Some embodiments further comprise microcrystalline cellulose/sodium carboxymethylcellulose. Some embodiments may include up to 25 mg/mL glycerin.

In some embodiments, the suspension comprises zonisamide; a suspending agent which is about 2 to about 3.5 mg/mL xanthan gum; a buffering agent which is citric acid monohydrate or disodium hydrogen phosphate; 0 to 25 mg/mL glycerin; and microcrystalline cellulose/sodium carboxymethylcellulose.

Some embodiments provide a pharmaceutical composition in the form of a suspension for oral delivery comprising an active pharmaceutical ingredient; water; a suspending agent; a stabilizing amount of wetting agent; and a buffering agent in an amount sufficient to make the composition pH about 3 to about 6.

Other embodiments will be apparent from this specification without departing from the scope and spirit of this disclosure.

EXAMPLES

The pharmaceutical composition of the present invention is explained in more detail with reference to the following examples. These examples are provided by way of illustration only and should not be construed as limit to the scope of the claims in any manner.

Example-1: A Liquid Oral Pharmaceutical Composition Comprising Zonisamide

TABLE 1

| ZONISAMIDE LIQUID COMPOSITION | |
|---|---|
| Ingredients | mg/ml |
| Zonisamide | 20.00 |
| Carboxymethylcellulose Sodium Dispersion) | 20.00 |
| Sodium benzoate | 2.00 |
| Xanthan gum | 3.50 |
| Citric acid monohydrate | pH 4-5 |
| Tri-sodium citrate dihydrate | pH 4-5 |
| Sucralose | 2.00 |
| Strawberry flavour | 0.10 |
| Purified water | Q.S to 1.0 ml |

Method of Preparation:

The process for the preparation of the liquid composition of Zonisamide involves dissolving required quantities of sodium benzoate, citric acid monohydrate, tri-sodium citrate and sucralose in purified water, followed by dispersing required quantities of Microcrystalline Cellulose & Carboxymethylcellulose Sodium Dispersion, xanthan gum, Zonisamide and Strawberry flavour separately in purified water, mixing both the mixtures, homogenizing it and making up the final volume to the required quantity of batch size with purified water.

Those who are skilled in the art can understand that variations in the above described process for the preparation of liquid compositions of the present invention can be adopted which are well within the skills of the skilled artisan. One can change sequences of the steps in the above mentioned process for the purposes of suitability and convenience without affecting the quality and characteristics of the resulting product.

Those who are reasonably skilled in the art can easily understand that similar liquid formulations using Zonisamide with other suitable excipients, mentioned in the foregoing paragraphs may be prepared in the above mentioned formula using above mentioned processes for the preparation. Such other examples of compositions and processes of preparation thereof are also within the ambit of the invention disclosed and claimed in the present application.

Example 2: Stability Studies of the Pharmaceutical Composition Prepared in Example 1

The oral liquid pharmaceutical composition prepared according to Example 1 exhibits unexpected stability profile when tested after one (1), three (3) and six (6) months under the conditions 40° C./25% RH and 25° C./40% RH. The liquid composition according to the present invention possess very less amount of impurities and highest degree of purity. The results of the stability tests conducted are summarized in the table below.

TABLE 2

STABILITY STUDY RESULTS OF ZONISAMIDE
LIQUID COMPOSITION OF EXAMPLE 1

| | | Results | | |
|---|---|---|---|---|
| | | 40° C./ 25% RH | | 25° C./ 40% RH |
| Parameters | Initial | 1 month | 3 months | 3 months |
| Description | White to Off white suspension | Complies | Complies | Complies |
| pH | 4.32 | 4.18 | 4.30 | 4.30 |
| Assay of Zonisamide (%) | 97.2 | 102.3 | 101.3 | 101.2 |
| Impurity A | ND | ND | ND | ND |
| Unknown Impurities (%) | 0.06 | 0.06 | 0.06 | 0.06 |
| Total Impurities (%) | 0.07 | 0.08 | 0.09 | 0.10 |

ND = Not Detected

Example 3: Zonisamide Suspension

A pharmaceutical composition in the form of a suspension for oral delivery comprises zonisamide; water; a suspending agent; and a buffering agent in an amount sufficient to make the composition pH about 3 to about 6. Exemplary compositions are discussed below:

TABLE 3

ZONISAMIDE ORAL SUSPENSION

| Sr. No. | Ingredients | Role of Ingredients | Prototype Formula % w/v | (mg/mL) |
|---|---|---|---|---|
| 1 | Zonisamide | Active | 2 | 20 |
| 2 | Microcrystalline cellulose and Carboxymethylcellulose sodium | Suspending agent | 2 | 20.00 |
| 3 | Sucralose | Sweetening agent | 0.2 | 2.00 |
| 4 | Xanthan gum | Suspending agent | 0.35 | 3.50 |
| 5 | Sodium Benzoate | Preservatives | 0.1 | 1.00 |
| 6 | Citric Acid monohydrate | Buffering agent | 0.3719 | 3.72 |
| 7 | Tri-Sodium Citrate Di-hydrate | Buffering agent | 0.3592 | 3.59 |
| 8 | Strawberry flavor | Flavoring agent | 0.01 | 0.10 |
| 9 | water | Vehicle | q.s to 100 ml | q.s to 1 ml |

1.0% active may also be used with the remaining excipient's concentration is same Example 4: Stability Studies of the Pharmaceutical Composition Prepared in Example 1

The oral liquid pharmaceutical composition prepared according to Example 1 exhibits an unexpected stability profile when tested after one (1), three (3) and six (6) months under the conditions 40° C./25% RH and 25° C./40% RH. The liquid composition according to the present invention possess very less amount of impurities and highest degree of purity. The results of the stability tests conducted are summarized in the table below.

TABLE 4

| | | Initial | 40/25-3M | 25/40-3M | 40/25-6M | 25/40-6M |
|---|---|---|---|---|---|---|
| 1 | Description | White to offwhite suspension | White to offwhite suspension | White to offwhite suspension | White to offwhite suspension | White to offwhite suspension |
| 2 | PH | 4.5 | 4.2 | 4.3 | 4.4 | 4.4 |
| 3 | Assay of zonisamide | 100.9 | 101.90% | 100.50% | 102.40% | 101.70% |
| | Assay of sodium benzoate | 89.8 | 100.90% | 94.60% | 101.40% | 99.80% |
| 4 | Impurity A | ND | ND | ND | ND | 0.01 |
| | Single max impurity | 0.05 | 0.06 | 0.06 | 0.05 | 0.05 |
| | Total impurities | 0.05 | 0.06 | 0.07 | 0.05 | 0.05 |

Methods of Treatment.

The pharmaceutical compositions disclosed herein are useful to treat a variety of conditions, diseases, disorders, or other ailments. In some embodiments, the solutions are meant to mimic their solid form counterparts, providing the same effectiveness in the same dose. In each case, the method of treating the condition, disease, disorder or other ailment comprises administering the suspension to a patient in need of such treatment to provide a desired or therapeutically acceptable dose of the active pharmaceutical ingredient.

The methods disclosed are for the treatment of a disease or a condition that can be treated by the active pharmaceutical ingredient in the solution. The method comprises administering to a patient, such as human, an effective dosage amount of a liquid pharmaceutical composition comprising the active pharmaceutical ingredient and one or more pharmaceutically acceptable excipients or additives as disclosed and described herein.

"Effective dosage amount" as used herein with respect to, for example liquid pharmaceutical compositions of the present invention shall mean that dosage that provides the specific pharmacological response for which the active pharmaceutical ingredient administered in a significant number of subjects in need of such treatment. It is emphasized that "effective dosage amount", administered to a particular subject in a particular instance will not always be effective in treating the diseases described herein, even though such dosage is deemed a "effective dosage amount" by those skilled in the art.

The liquid pharmaceutical compositions of the present invention are proposed to have unexpectedly dramatic dissolution profiles. Rapid dissolution of an administered active agent is preferable, as faster dissolution generally leads to greater bioavailability and faster onset of action. To improve the dissolution profile and bioavailability of the active it would be useful to increase dissolution of the active used so that it could attain a level close to 100% dissolution of the drug substance.

The liquid pharmaceutical compositions of the present invention comprising the active pharmaceutical ingredient or salt thereof or derivative thereof, exhibit improved or comparable pharmacokinetic profiles as compared to marketed or known compositions of the same active pharmaceutical ingredient or salt or derivative thereof. For example, the Cmax and/or AUC of the liquid pharmaceutical compositions of disclosed herein can be greater than or substantially equal to the Cmax and/or AUC for known or marketed compositions, e.g. solid formulations, administered at the same dose. In addition, the Tmax of the liquid compositions of the present invention can be lower than or substantially equal to that obtained for a known or marketed compositions, administered at the same dose. In addition, combinations of an improved or comparable Cmax, AUC and Tmax profile can be exhibited by the liquid compositions of the invention, as compared to known or marketed compositions. In further aspects, the liquid compositions of the present invention may result in minimal different absorption levels when administered under fed as compared to fasting conditions.

The liquid compositions exhibit in comparative pharmacokinetic testing with marketed or known formulations, administered at the same dose, a Tmax not greater than about 90%, not greater than about 80%, not greater than about 70%, not greater than about 60%, not greater than about 50%, not greater than about 30%, not greater than about 25%, not greater than about 20%, not greater than about 15%, not greater than about 10%, or not greater than about 5% of the Tmax exhibited by the marketed or known formulation.

In some embodiments, the liquid compositions exhibit in comparative pharmacokinetic testing with marketed or known formulation, administered at the same dose, a Cmax which is at least about 50%, at least about 100%, at least about 200%, at least about 300%, at least about 400%, at least about 500%, at least about 600%, at least about 700%, at least about 800%, at least about 900%, at least about 1000%, at least about 1100%, at least about 1200%, at least about 1300%, at least about 1400%, at least about 1500%, at least about 1600%, at least about 1700%, at least about 1800%, or at least about 1900% greater than the Cmax exhibited by the marketed or known formulation.

In one of the further aspects, the liquid compositions of the present invention exhibit in comparative pharmacokinetic testing with marketed or known formulation, administered at the same dose, an AUC which is at least about 25%, at least about 50%, at least about 75%, at least about 100%, at least about 125%, at least about 150%, at least about 175%, at least about 200%, at least about 225%, at least about 250%, at least about 275%, at least about 300%, at least about 350%, at least about 400%, at least about 450%, at least about 500%, at least about 550%, at least about 600%, at least about 750%, at least about 700%, at least about 750%, at least about 800%, at least about 850%, at least about 900%, at least about 950%, at least about 1000%, at least about 1050%, at least about 1100%, at least about 1150%, or at least about 1200% greater than the AUC exhibited by the marketed or known formulation.

In some embodiments, the Tmax of the active pharmaceutical ingredient or salt thereof used for the preparation of the liquid composition according to the present invention, when assayed in the plasma of the mammalian subject, is less than about 6 to about 8 hours. In other aspects of the invention, the Tmax of the active or salt thereof is less than about 6 hours, less than about 5 hours, less than about 4 hours, less than about 3 hours, less than about 2 hours, less than about 1 hour, or less than about 30 minutes after administration.

In some aspects, the liquid compositions exhibit improved or comparable bioavailability as compared to known or marketed compositions.

The liquid pharmaceutical compositions of the present invention are suitable for use in the industry.

It should be understood that various changes and modifications to the presently preferred embodiments, examples and processes described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. A liquid oral pharmaceutical suspension, comprising: zonisamide in an amount of about 20 mg/mL; a suspending agent comprising about 2 mg/mL to about 3.5 mg/mL xanthan gum and about 20 mg/mL of a combination of microcrystalline cellulose and sodium carboxymethylcellulose; one or more buffering agents; and one or more pharmaceutically acceptable excipients, wherein the one or more pharmaceutically acceptable excipients comprise a preservative; wherein the liquid oral pharmaceutical suspension has a pH of 3.5 to 5.0, wherein the composition is stable for at least 6 months when stored at 40° C. and 25% relative humidity.

2. The liquid oral pharmaceutical composition according to claim 1, wherein the one or more buffering agents are selected from the group consisting of sodium acetate, sodium citrate, ammonium sulfate, sodium phosphate, disodium hydrogen phosphate, potassium citrate, citric acid monohydrate, trisodium citrate dihydrate, and combinations thereof.

3. The liquid oral pharmaceutical suspension according to claim 1, further comprising one or more sweetening agents, one or more flavoring agents, one or more vehicles, or combinations thereof.

4. The liquid oral pharmaceutical composition according to claim 1, wherein the preservative is selected from the group consisting of benzyl alcohol, chloro-butanol, chlorocresol, alkyl esters of paraben, phenol, phenyl ethanol, propylene glycol, chloroform, benzoic acid, potassium sorbate, sodium benzoate, and combinations thereof.

5. The liquid oral pharmaceutical suspension according to claim 3, wherein the one or more sweetening agents are selected from the group consisting of sucralose, sucrose, glycerol, liquid glucose, sorbitol, maltitol, saccharin sodium, aspartame, and combinations thereof.

6. The liquid oral pharmaceutical composition according to claim 3, wherein the one or more flavoring agents are selected from the group consisting of essential oils, fruit flavors, and combinations thereof.

7. The liquid oral pharmaceutical suspension according to claim 6, wherein the essential oil is selected from the group consisting of peppermint oil, orange oil, lemon oil and combinations thereof.

8. The liquid oral pharmaceutical suspension according to claim 6, wherein the fruit flavour is selected from the group consisting of peppermint flavour, raspberry flavour, strawberry flavour, tutti-fruit flavour, and combinations thereof.

9. The liquid oral pharmaceutical suspension according to claim 3, wherein the one or more vehicles are aqueous vehicle selected from the group consisting of purified water, hydro alcoholic, a polyhydric alcohol, a buffer, and combinations thereof.

10. The liquid oral pharmaceutical composition according to claim 1, wherein the composition has a single max impurity of 0.06% or less and total impurities of 0.10% or less.

11. The liquid oral pharmaceutical composition according to claim 1, wherein the composition exhibits less than 0.05% of impurity A and less than 0.25% of total impurity.

12. The liquid oral pharmaceutical suspension of claim 1, wherein the one or more buffering agents comprise citric acid monohydrate and tri-sodium citrate dihydrate.

13. The liquid oral pharmaceutical suspension according to claim 1, comprising:

zonisamide in an amount of about 20 mg/mL;

xanthan gum in an amount of about 3.5 mg/mL;

a combination of microcrystalline cellulose and sodium carboxymethylcellulose in an amount of about 20 mg/mL;

sodium benzoate in an amount of about 1.0 mg/mL;

one or more buffering agents comprising citric acid monohydrate and tri-sodium citrate dihydrate;

one or more sweetening agents;

one or more flavoring agents; and purified water.

* * * * *